United States Patent [19]

Cobia et al.

[11] Patent Number: Plant 7,175

[45] Date of Patent: Feb. 27, 1990

[54] PLANT OF THE CACTACEAE PLANT FAMILY

[75] Inventors: Barnell L. Cobia, Winter Garden; Mark E. Cobia, Orlando, both of Fla.

[73] Assignee: B. L. Cobia, Inc., Winter Garden, Fla.

[21] Appl. No.: 281,808

[22] Filed: Dec. 9, 1988

[51] Int. Cl.[4] ..... A01H 5/00

[52] U.S. Cl. ..... Plt./88

[58] Field of Search ..... Plt./88

*Primary Examiner*—Robert E. Bagwill

*Attorney, Agent, or Firm*—Roger L. Martin

[57] ABSTRACT

A new and distinct plant variety of the Cactaceae family is of the type known commercially as a "Christmas Cactus" and has a growth habit which is similar to that of the "Kris Kringle" variety (U.S. Plant Pat. No. 3,688) but which, nevertheless, differs, among other things, by having phylloclades with thicker and wider wings and with thicker and longer teeth, and sterile flowers with shorter perianth tubes and tube laminating and forming tepals that have generally wider blades.

4 Drawing Sheets

The invention relates to a new and distinct plant variety of the Cactaceae family and which has been named the *Zygocactus truncatus* 'Kris Kringle II' by the inventors.

Certain plant varieties of the Cactaceae family are well known in the foliage plant market and among these are those which are commonly referred to as the Christmas Cactus varieties because they tend to bloom during the Thanksgiving–Christmas holiday season in the northern hemisphere. The Christmas Cactus varieties on the market have blooms which vary in color from one variety to the next as is evident from the current U.S. patent art. One of the more popular varieties is sold commercially in the market place is the variety that has been named *Zygocactus truncatus* "Kris Kringle". The variety has a "reddish" colored bloom and forms the subject matter of U.S. Plant Pat. No. 3,688.

SUMMARY OF THE INVENTION

A general objective has been to develop a new plant variety with a "reddish" colored bloom and which is distinguishable from the "Kris Kringle" variety and capable of being marketed in competition therewith. The objective has been fully realized by the development of the new plant variety hereinafter described in detail. The new plant variety was developed in a nursery located at Winter Garden, Fla., as a hybrid secured by cross-pollinating the flower of an unnamed research variety (ZH3990-T) with pollen from the flower of yet another unnamed research variety (ZH6658). The seeds taken from the fertilized seed pod where cultivated at the mentioned nursery location and after prolonged observation of the seedlings the hybridized plant of the new variety was selected and asexually reproduced by the propagation of cuttings taken from the original hybrid.

The maternal variety is similar in growth habit to the new plant variety but the bloom colors on the plant specimens of the material variety can be generally described as less intense than those of the new plant variety. The patented "Kris Kringle" variety was the maternal parent of the paternal parent of the new plant variety and specimens of the paternal parent of the new plant variety have smaller foliage and blooms than specimens of the patented "Kris Kringle" plant variety. The bloom colors on the plant specimens can also be described as less intense than those of the "Kris Kringle"

variety. Both parents of the new plant variety are fertile whereas the new plant variety is sterile.

Through successive propagations of cuttings taken from the mutated plant part, it has been ascertained that specimens of the new plant variety generally resemble the "Kris Kringle" variety in most respects but are distinguishable from this variety and from other related varieties known to the inventors by a growth habit which is evident in plant specimens of the new variety that have been propagated and grown under nursery conditions utilized in the growing of tropical plants in Winter Garden, Fla., as combining the following principal characteristics:

1. An erect growth habit,
2. Phylloclades which, in comparison to the Kris Kringle variety, have (a) wings with greater thickness and width dimensions and (b) teeth with greater thickness dimensions and longer areole to apex dimensions,
3. Flowers which, in comparison to the Kris Kringle variety, are sterile and have (a) a sepaloid series of tepals with a smaller number of tepals that generally have shorter length dimensions and smaller maximum blade width dimensions, (b) a tube laminating series of tepals that generally have greater maximum blade width dimensions, (c) a tube forming series of tepals that generally have greater maximum blade width dimensions and perianth tubes that generally have shorter length dimensions, (d) an androecium with a smaller number of tube attached stamens, and (e) a gynoecium with a shorter style length dimension and longer ovary length dimension.

BRIEF DESCRIPTION OF THE DRAWINGS

The accompanying drawings serve by color photographic means to illustrate the new plant variety and wherein one sheet shows a ten (10) month old specimen which was grown from the propagation of a single phylloclade in a conventional 3" pot found in the marketplace. A second sheet shows an enlargement of a fully open bloom taken from the specimen shown in previously mentioned sheet. Still another sheet shows a bloom as sectioned generally longitudinally through the perianth tube and ovary to expose the style and stamen arrangement. The last sheet shows three phylloclades taken from a specimen of the new variety, each phylloclade having an attached bud or bloom and illustrating the buds in progressing stages of maturity.

DETAILED PLANT DESCRIPTION

The following is a detailed description of the new plant variety with colors and hues, unless otherwise clearly indicated by the text as, for example, through the absence of color notations, being named in accord with the ISCC-NBS Method of Designating Colors (U.S. Dept. of Commerce, National Bureau of Standards, Circular 553), the named colors being interpreted from color notations derived by comparison with the color specimens of the Munsell Book of Color. The description is further based on observations of well fertilized plants of about one year of age from initial propagation which were grown under 50–70% shaded glasshouse nursery conditions in the Winter Garden, Fla. area and wherein temperatures range from 60°–85° F. during the winter months, from 75°–95° F. during the summer months, and are ambient during the intervening periods.

I. Name: *Zygocactus truncatus* 'Kris Kringle II'.

II. Parentage:

A. *Maternal.*—An unnamed and unmarketed fertile research variety that is similar in apparent growth habit to the subject new plant variety but with bloom colors that are less intense.

B. *Paternal.*—An unnamed and unmarketed fertile research variety having a heritage that includes the patented "Kris Kringle" variety as the maternal parent and having an apparent growth habit which is similar to the "Kris Kringle" variety but which provides specimens that are less erect, generally smaller foliage and blooms and bloom colors that are less intense.

III. Classification:

A. *Botanic* (*Britton and Rose, The Cactaceae*, Constable and Co., Ltd., London 1937, Vol. IV)-.—(1) Family: Cactaceae. (2) Tribe: Cereeae. (3) Sub-Tribe: Epiphyllanae. (4) Genus: Zygocactus. (5) Species: *truncatus* (Haworth) Schumann.

B. *Commercial.*—Thanksgiving–Christmas blooming cactus.

IV. Form: Epiphylic and terrestrial shade loving, succulent, leafless plant with jointed and branched stems.

V. Stems:

A. *General.*—Irregular with usually multichotomous branching of both upright and pendulous, adventitiously rootable, flattened phylloclades that have a prominent midrib and prominently toothed lateral wings.

B. *Phylloclades.*—(1) General: Elongated and flat with a transversely elongated, areole bearing, truncated apex, with inwardly tapering basal wing margins that merge with a usually broadly pointed basal juncture with the phylloclade therebelow, and with an axially located areole usually being associated with each tooth. (2) Midrib: (a) General — Extends longitudinally of phylloclade and continuously through joints and with a laterally tapering cortex at the wing insertions. Pith surrounding vascular bundles that branch and provide lateral extensions of the vascular system to the marginal teeth. (b) Texture — Smooth, waxy epidermis with wax in small embedded scales and becoming woody in basal stem areas with specimen aging. (c) Size (at maturity) — 1. Length: Usually 25–41 mm. 2. Thickness: Usually 2–6.5 mm. (d) Color (at maturity) — Usually dominated by a yellow green and/or olive green hue. Commonly moderate yellow green (7.5 GY 5/6) and/or moderate olive green (7.5 GY 4/6). (3) Wings: (a) General — Dentate and generally flattened from midrib cortex to tooth insertions and with slight thinning taper toward margins. (b) Margins — Toothed. (c) Texture — Succulent to leathery with smooth, waxy epidermis where the wax is arranged in small embedded scales of higher density than in midrib area, and becoming corky in the basal stem areas with specimen aging. (d) Size (at maturity) — 1. Thickness: About 1–3 mm in the area intermediate the margin and midrib. 2. Width: Usually 11–22 mm as measured from phylloclade axis to most offset lateral areole. 3. Color (at maturity) — Usually dominated by an olive green hue. Commonly moderate olive green (7.5 GY 3/4) (7.5 GY 4/4) (7.5 GY 4/6). (4) Teeth: (a) Shape — 1. General: Generally flattened and tapered along the margins and from the wing insertion to an apex having a hyaline, single cell, pointed spine with non-predictable bending. 2. Abaxial margin: Usually straight to convex. 3. Adaxial margin: Usually straight to concave. (b) Orientation — Generally project distally of phylloclade in an alternate arrangement. (c) Margins — Entire. (d) Texture — Succulent to leathery with smooth waxy epidermis having wax in small embedded scales of density comparable to wings, and becoming corky in basal stem areas with specimens aging. (e) Size (at maturity)— 1. Thickness: Usually 0.5–1.5 mm in center area. 2. Areole to apex dimension (adaxial marginal side): Usually 3–11 mm in the upper quadrants of the phylloclades. (f) Number — 5–8 per phylloclade. (g) Color — Usually dominated by an olive green hue. Commonly moderate olive green (7.5 GY 3/4) (7.5 GY 4/4) (7.5 GY 4/6). (5): Areoles: (a) Terminal areole — Large, elongated, oval shaped with several acicular bristles, and several buds that may mature into either new phylloclades or flowers. The opposite ends of the areole are located adjacent to subsidiary areoles which are in turn located at the axils of the teeth at the distal end of the phylloclade. (b) Axillary aeroles — Acicular bristles without glochida but having copious, short, brownish, multicellular, wooly hairs. In areoles located below the teeth at the distal end of the phylloclade, there is usually only one areole which is frequently latent.

VI. Buds: Unarmored, ovoid and chlorophyllous.

VII. Flowers:

A. *General.*—Sessile, zygomorphic, usually solitary, terminal, perfect and epigynous with double hypanthium and whorled tepals (undifferentiated sepals and petals) having a spiral emergence as a perianth provided with a sepaloid series of free tepals, a tube laminating series of tepals, and a tube forming series of united tepals.

B. *Sepaloid series.*—(1) General: Free tepals inserted on top of ovary. (2) Shape: Deltoid in outer members of whorl and grading inwardly in the whorl to provide progressively greater length dimensions and broader apices. All members have a pointed tip and entire margins with sparse irregular teeth appearing mainly in the apex areas of the inner members of the whorl. (3) Texture: Succulent and glabrous outer whorl members and grading inwardly in whorl to silken blades with fleshy basal areas. (4) Number: Usually 4–7. (5) Size (at full bloom): (a) Length (base-tip dimension) — Usually less than 15 mm. (b) Width (maximum) — Usually less than 8 mm. (6) Color (at full bloom): Varies from the outer members to the inner members with the smallest outer whorl tepals usually having a continuous field that in color is dominated by a yellow green hue. The inner whorl tepal members have a continuous marginal and center blade area that in color is usually dominated by a red and/or pink hue and which merges proximally with a translusent white basal area. Commonly deep pink (5 R 6/10), and/or strong red (5 R 5/12) in the continuous marginal and center blade areas of the inner whorl tepal members. Commonly light yellow green (5 GY 8/6) and/or strong yellow green (5 GY 7/10) in the basal areas of the outer whorl members. (7) Orientation: Erect to recurve at full bloom.

C. *Tube laminating series.*—(1) General: Tepals inserted on ovary and basally united below the throat as outer laminations on the perianth tube and with progressively greater amount of basal fusion inwardly in the whorl. (2) Shape: Zygomorphic and grading inwardly in the whorl with progressively greater length dimensions and broader apices so that the blade area changes inwardly in the whorl from ovate with an acute tip to spatulate with a broader acute tip. Entire margins with sparse, irregular teeth mainly in apex areas. (3) Texture: Succulent and glabrous outer whorl members and grading inwardly to silken blades with slightly fleshy basal areas. (4) Number: Usually 11–13 tepals. (5) Size (at full bloom): (a) Length (base-tip dimensions) — Usually ranging from about 13 to about 61 mm. (b) Width (maximum) — Usually ranging from about 8 to about 20 mm. (6) Color (at full bloom): (a) General — Tepals with a basal area that is usually a transluscent white immediately above the insertion and with a continuous marginal and center blade area that in color is dominated by a red, reddish orange, and/or pink hue and which merges proximally with the color in the basal area of the tepal. (b) Basal area — Translucent and white at insertion and occassionally showing random trace areas of light yellow green (5 GY 9/6) and/or brilliant yellow green (5 GY 8/8) in the outer whorl members. (c) Blade area — Commonly deep pink (5 R 6/10), strong reddish orange (7.5 R 5/12), strong red (5 R 5/12) and/or vivid red (5 R 4/14) in the continuous marginal and center blade area. (7) Orientation: Perpendicular to recurve at full bloom.

D. *Tube forming series.*—(1) General: Tepals basally united to form hollow perianth tube that is inserted on ovary and equipped at its throat with an irregular carina (keel). (2) Shape: (a) Perianth tube — Elongated and elipsoidal in cross section with the major ellipsoidal axis usually generally normal to the plane of the supporting phylloclade. (b) Blades — Nearly zygomorphic and thinly spatulate with acute tips and entire margins having sparse irregular teeth in apex area. (c) Carina (keel) — Irregular and transcending. (3) Texture: (a) Perianth tube — Thick, succulent and slightly ribbed. (b) Blades — Translucent and silken. (c) Carina (keel) — Fleshy. (4) Number: Usually 8–9. (5) Size (at full bloom): (a) Perianth tube — 1. Length (base-keel): Usually 25–31 mm along tube axis. 2. Major axis: Usually 8–14 mm at throat interior. 3. Minor axis: Usually 5–10 mm at throat interior. (b) Blades — 1. Length (keel-tip): Usually 30–39 mm. 2. Width (maximum): Usually 13–21 mm. (6) Color (at full bloom): (a) Perianth tube — A basic field that is translucent white with longitudinally extending, randomly arranged striations or streaks that in color are commonly purplish white (5 RP 9/1). (b) Blades — A continuous marginal and center blade area distally of the keel that in color is dominated by a red and/or reddish orange hue and which merges with a basal area distally of the keel that is usually translucent white. Commonly vivid red (5 R 4/14), strong red (5 R 5/12), moderate reddish orange (7.5 R 6/10) and/or strong reddish orange (7.5 R 5/12) in the continuous marginal and center blade area of the blade. Commonly white, purplish white (5RP 9/1) and/or color dominated by pale purplish pink (5 RP 9/2) in the basal area distally of the keel. (c) Carina (keel) — Color usually dominated by a purplish pink and/or purplish red hue. Commonly deep purplish pink (5 RP 6/10) and/or moderate purplish red (5 RP 5/10). (7) Orientation: Acute to recurve.

E. *Androecium (stamens).*—(1) General: Numerous exserted and diadelphous stamens with one group having filaments basally fused to the perianth tube and the other group having filaments basally united to form a nectary housing, thin annulus around the style and which is provided with thin, deflexed, irregular, toothed margin or ruffle at the throat of the annulus. (2) Stamen number: (a) Tube attached group — Usually 61–74. (b) Basally united group — Usually 17–21. (3) Filaments: (a) General — Translucent with another connective. (b) Shape — Long, slender, terate. (c) Texture — Glabrous and capillaceous. (d) Color — Usually translucent white over entire length. (e) Size (at full bloom) — 1. Length: a. Tube attached group — Usually 39–53 mm. b. Basally united group — Usually 33–46 mm. 2. Diameter: Usually about 0.25 mm intermediate opposite ends. (4) Anthers: (a) General — Adnate with four longitudinally dehiscent pollen sacs and connective inserted at end. (b) Shape — Elongated. (c) Texture — Waxy. (d) Color (before dehiscence) — Dominated by a yellow hue. Commonly light yellow (5 Y 9/6) (2.5 Y 9/6). (e) Sterility — Sterile.

F. *Gynoecium (pistil).*—(1) General: Exserted with compound, pariental placentation and united style surrounded by annular diffuse yellowish nectary at its insertion. (2) Style: (a) General — Hollow, stout and inserted at ovary. (b) Shape — Elongated and terete. (c) Texture — Fleshy and smooth. (d) Color — Usually dominated by a reddish purple and/or purplish red hue at the proximal end of the style and by a reddish purple hue at the distal end. Commonly moderate purplish red (5 RP 5/10) and/or strong reddish purple (2.5 RP 5/10) at proximal end and strong reddish purple (2.5 RP 4/10) at distal end. (e) Size (at full bloom) — 1. Length: Usually 48–57 mm. 2. Diameter: Usually 0.5–1.0 mm intermediate opposite ends. (3) Stigma: (a) General — Exserted and erect with usually 6–9 inner marginally adhering lobes. (b) Shape — Elongated and tapered toward lobe tips and having relatively blunt apices. (c) Texture — Fleshy and smooth with inner sides of lobes having short glutinous capillaceous hairs. (d) Color — Usually dominated by a reddish purple hue. Commonly strong reddish purple (2.5 RP 5/10) (2.5 RP 4/10). (e) Size — 1. Length: Usually 3–6 mm along inner margins. (4) Ovary: (a) General — Inferior with thin epidermis and usually 5–8 carpules with numerous ovules. (b) Shape — Terete to ovoid and generally broadening from insertion to floral end. Ribbed single concavity with inserted style. (c) Texture — Succulent with glabrous thin outer epidermis. (d) Color — A basic field with color usually dominated by a yellow green hue. Commonly brilliant yellow green (5 GY 8/8) and/or strong yellow green (5 GY 7/10) (5 GY 6/8) (2.5 GY 7/8) (2.5 GY 6/8). (e) Size — 1. Length: Usually 8–12 mm from insertion to cavity base. 2. Major axis: Usually 9–10 mm at distal end of concavity. 3. Minor axis: Usually about 7–9 mm at distal end of concavity.

VIII. Growth Habit: Erect.

General Description of a Plant Specimen

Age of plant: Nine (9) months from initial propagation of single phylloclade.

Branches from propagated phylloclade: Three (3).

Total number of new phylloclades grown: Seventeen (17).

GENERAL:

| Branch No. | No. of Phylloclades | Maximum Branch Length | No. of Tips |
|---|---|---|---|
| 1 | 6 | 123 mm | 2 |
| 2 | 7 | 143 mm | 2 |
| 3 | 4 | 61 mm | 2 |

MIDRIBS:

| Branch No. | Average Midrib Length | Average Midrib Thickness |
|---|---|---|
| 1 | 30.2 mm | 3.8 mm |
| 2 | 33.3 mm | 4.2 mm |
| 3 | 27.0 mm | 2.8 mm |

WINGS:

| Branch No. | Average Wing Width (Maximum) | Average Wing Width (Minimum) |
|---|---|---|
| [illegible] | [illegible] | [illegible] |

Phylloclade color: Moderate olive green (7.5 GY 4/4) (7.5 GY 4/6) and moderate yellow green (7.5 GY 5/6).

General Description of a Flower

The following is a general description of a flower of the new plant variety and which bloomed in December on a 9 month old plant specimen grown under shaded greenhouse nursery conditions in Winter Garden, Fla.

No. of buds and blooms on plant specimen: 8.

Bloom life: 8 days.

Sepaloid series of tepals:

*Number.*—5.

*Tepal size (at full bloom).*—Maximum base-tip dimension: 14 mm. Minimum base-tip dimension: 5 mm. Maximum width dimension: 8 mm.

*Color (at full bloom).*—Light yellow green (5GY 8/6) in the continuous field of the small outer whorl tepal members. Deep pink (5 R 6/10) and strong red (5 R 5/12) in the continuous marginal and center blade area, and light yellow green (5 GY 8/6) and translucent white in the basal areas of the inner whorl members.

Tube laminating series of tepals:

*Number.*—12.

*Size (at full bloom).*—Maximum base-tip dimension: 59 mm. Minimum base-tip dimension: 12 mm. Maximum blade width: 18 mm. Minimum blade width: 8 mm.

*Color.*—Deep pink (5 R 6/10), vivid red (5 R 4/4) and strong red (5 R 5/12) in the continuous marginal and center blade area of the blades and transluscent white in the basal areas of the blades.

Tube forming series of tepals:

*Number.*—9.

*Size (at full bloom).*—Periant tube: Length (base to keel) — 30 mm along tube axis. Major axis — 14 mm at throat interior. Minor axis — 8 mm at throat interior. Blades: Maximum length (keel-tip) — 38 mm. Minimum length (keel-tip) — 34 mm. Maximum blade width — 20 mm. Minimum blade width — 18 mm.

*Color.*—Periant tube: A basic field that is generally transluent white with random striations of purplish white (5 RP 9/1). Blade: Transluscent white in basal areas distally of the keel and vivid red (5 R 4/14), strong red (5 R 5/12) and strong reddish orange (7.5 R 5/12) in the continuous marginal and center field area of the blades.

Androecium:

*Stamen number.*—Tube attached group: 72. Basally united group: 20.

*Filaments.*—Color: translucent white.

*Size (at full bloom).*—Length — Tube attached group: 47 mm (avg). Basally united group: 38 mm (avg). Diameter: About 0.25 mm intermedi- [illegible]

[illegible]

*Anthers.*—Color: Moderate purplish red (5 RP 5/10) [illegible] (5 RP [illegible]) [illegible] — 5 mm. Diameter — 1.5 mm [illegible]

*Ovary.*—Color: Brilliant yellow green (5 GY 8/8) and strong yellow green (5 GY 7/10) (5 GY 6/8). Size (at full bloom): Length (insertion to concavity base) — 11 mm. Major axis — 10 mm at distal end of concavity. Minor axis — 8 mm at distal end of concavity.

We claim:

1. A new and distinct plant variety of the Cactaceae family as shown and described and which is mainly distinguished from its antecedents and known related varieties by a growth habit which is similar to that of the "Kris Kringle" variety but as modified by the combination of the following characteristics:

(1) An erect growth habit, (2) Phylloclades which, in comparison to the Kris Kringle variety, have (a) wings with greater thickness and width dimensions and (b) teeth with greater thickness dimensions and longer areole to apex dimensions, (3) Flowers which, in comparison to the Kris Kringle variety, are sterile and have (a) a sepaloid series of tepals with a smaller number of tepals that generally have shorter length dimensions and smaller maximum blade width dimensions, (b) a tube laminating series of tepals that generally have greater maximum blade width dimensions, (c) a tube forming series of tepals that generally have greater maximum blade width dimensions and perianth tubes that generally have shorter length dimensions, (d) an androecium with a smaller number of tube attached stamens, and (e) a gynoecium with a shorter style length dimension and longer ovary length dimension.

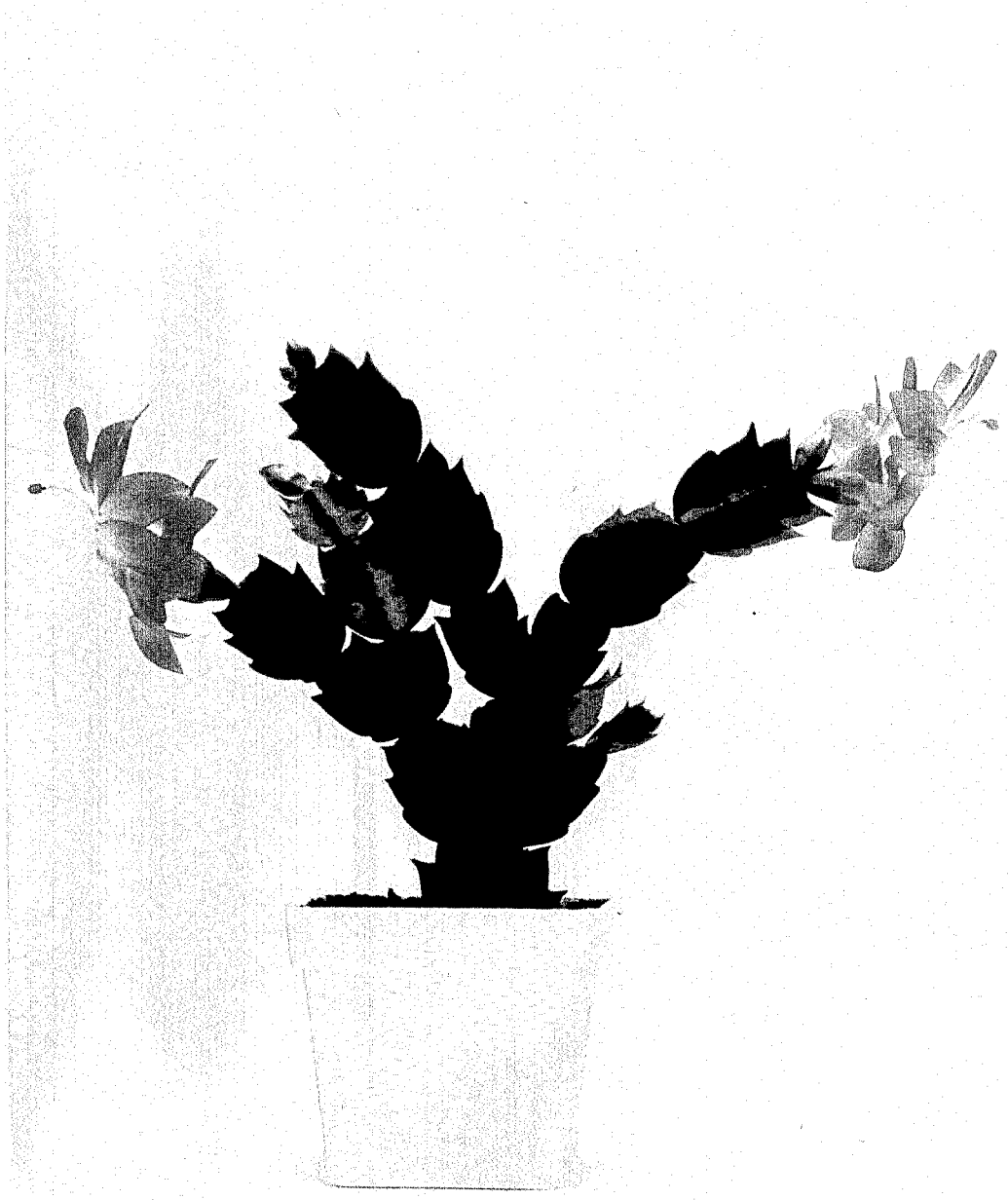

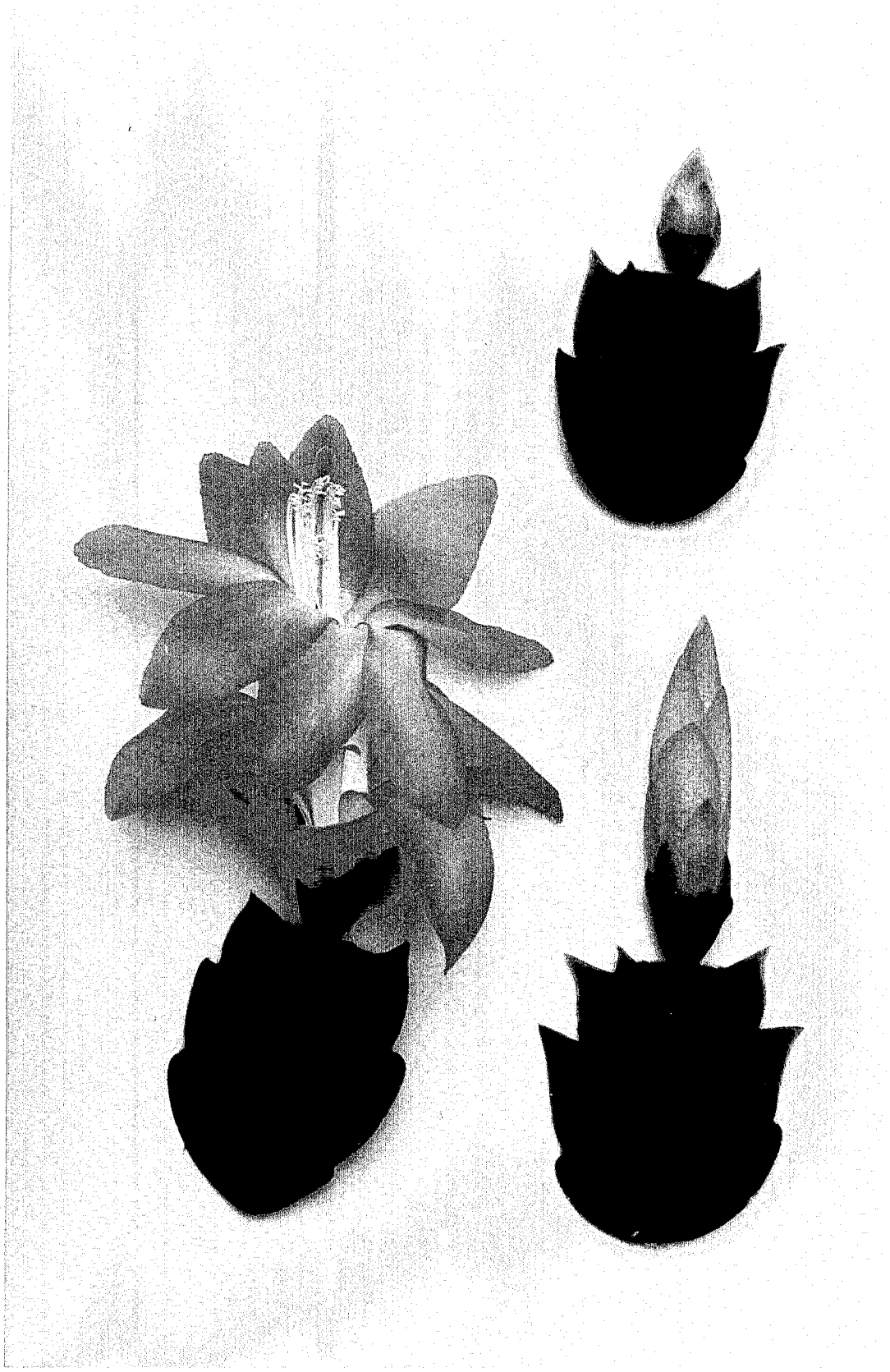

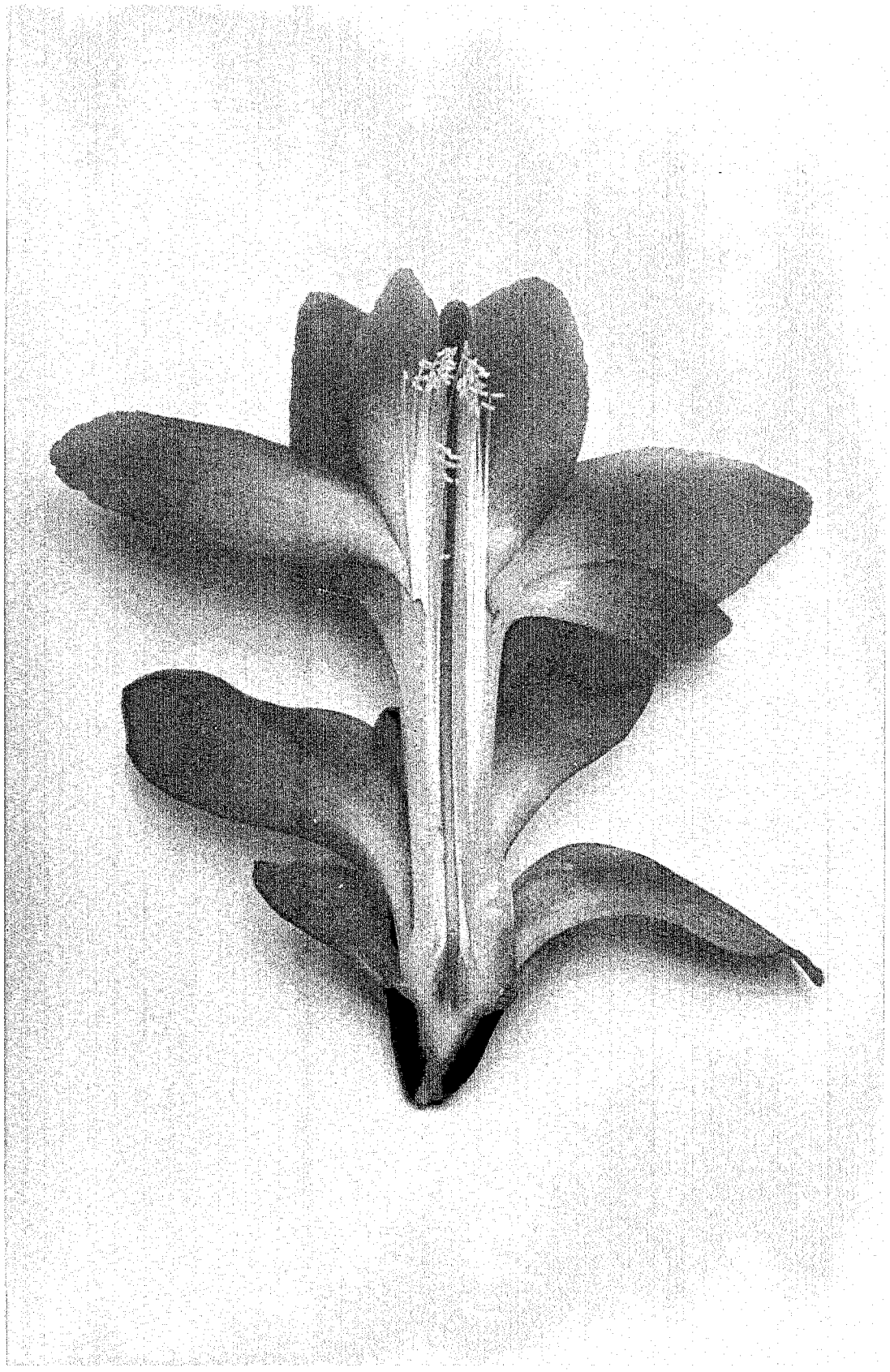

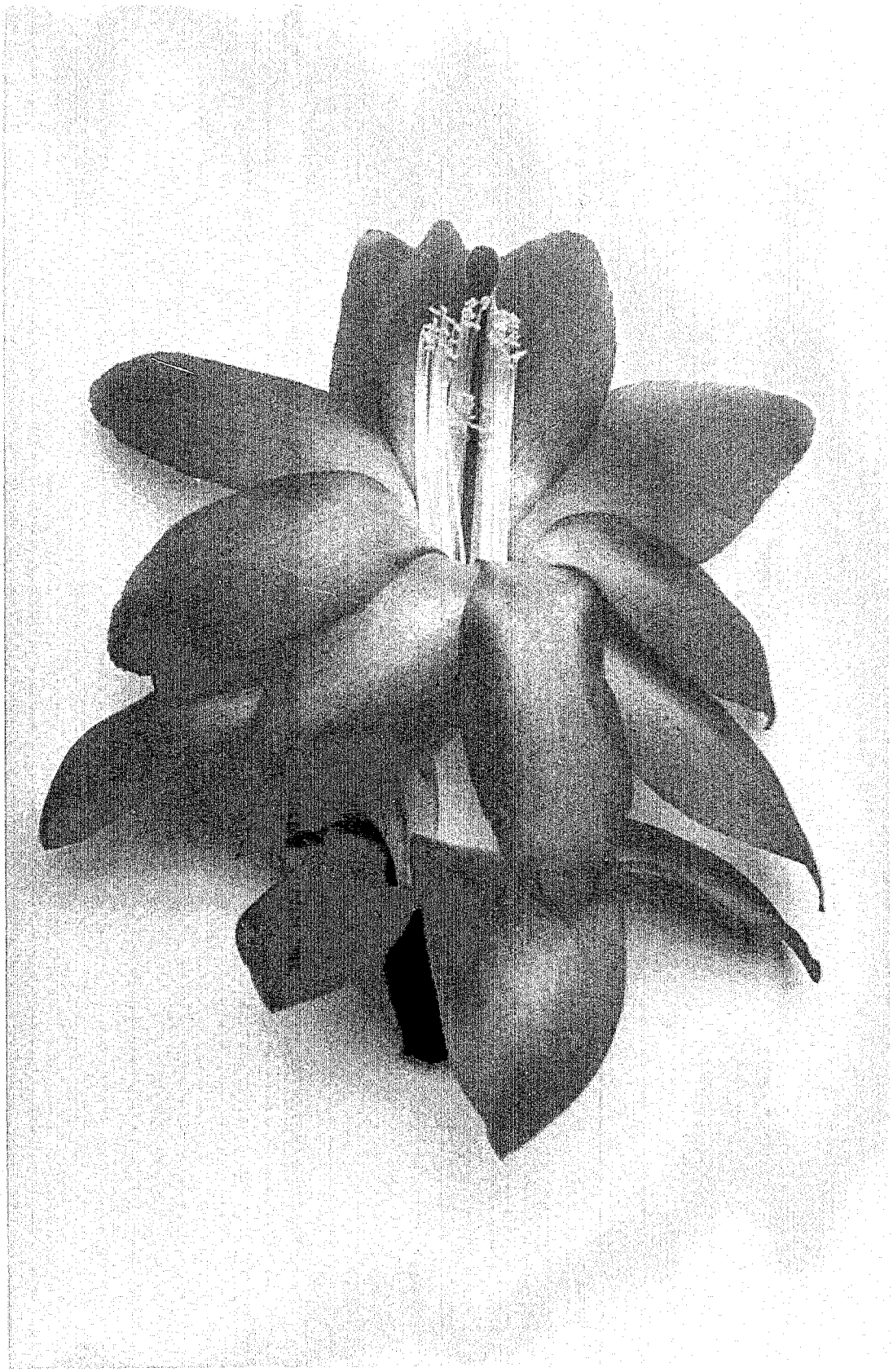

* * * * *